United States Patent [19]
Pollmann et al.

[11] Patent Number: 5,434,054
[45] Date of Patent: Jul. 18, 1995

[54] DEVICES FOR DETERMINING HYDROLASE ACTIVITY THROUGH ITS HYDROLYTIC RELEASE OF AN IMMOBILIZED INDICATOR ENZYME

[75] Inventors: Klaus Pollmann, Neulussheim; Helmut Freitag, Weinheim; Anselm Rothe, Birkenau, all of Germany

[73] Assignee: Boehringer Mannheim GmbH, Mannheim, Germany

[21] Appl. No.: 67,809

[22] Filed: May 27, 1993

[30] Foreign Application Priority Data

May 27, 1992 [DE] Germany .................. 42 17 474.0

[51] Int. Cl.⁶ .................................. G01N 33/53
[52] U.S. Cl. .................................. 435/7.92; 435/7.9; 435/7.91; 435/7.94; 435/18; 435/19; 435/22; 435/23; 435/24; 435/962; 435/966; 435/969; 435/970; 436/518; 436/528; 436/529; 436/530
[58] Field of Search .................. 422/56, 58, 60; 435/7.90, 7.91, 7.92, 7.94, 18–24, 962, 966, 969, 970; 436/528–530, 810, 518

[56] References Cited

U.S. PATENT DOCUMENTS

| | | | |
|---|---|---|---|
| 4,066,509 | 1/1978 | Ceska | 435/22 |
| 4,098,876 | 7/1978 | Piasio et al. | 424/1 |
| 4,144,306 | 3/1979 | Figueras | 422/56 |
| 4,331,590 | 5/1982 | Bocuslaski et al. | 435/7.91 |
| 4,446,232 | 5/1984 | Liotta | 435/7.92 |
| 4,590,157 | 5/1986 | Chandler et al. | 435/7.92 |
| 4,692,404 | 9/1987 | Ashihara et al. | 435/22 |
| 4,828,982 | 5/1989 | Wagner | 435/18 |
| 4,839,297 | 6/1989 | Freitag et al. | 422/56 |
| 4,874,710 | 10/1989 | Piran | 436/518 |
| 4,952,495 | 8/1990 | Belly et al. | 435/18 |
| 4,962,024 | 10/1990 | Schulte | 435/18 |
| 5,093,081 | 3/1992 | Sudo et al. | 422/56 |
| 5,190,864 | 3/1993 | Giese et al. | 435/7.9 |
| 5,215,885 | 6/1993 | Marrujo et al. | 435/7.9 |

FOREIGN PATENT DOCUMENTS

| | | | |
|---|---|---|---|
| 0060123 | 9/1932 | European Pat. Off. | |
| 0027036 | 4/1981 | European Pat. Off. | |
| 0075379 | 3/1983 | European Pat. Off. | |
| 0146866 | 7/1985 | European Pat. Off. | |
| 0244932 | 11/1987 | European Pat. Off. | |
| 0347256 | 12/1989 | European Pat. Off. | 435/7.91 |
| 0347839 | 12/1989 | European Pat. Off. | |
| 9000252 | 1/1990 | European Pat. Off. | |
| 0373908 | 6/1990 | European Pat. Off. | |
| 0518557 | 12/1992 | European Pat. Off. | |
| 3029579 | 2/1982 | Germany . | |
| 3247608 | 7/1984 | Germany . | |

OTHER PUBLICATIONS

Progress in Clinical Biochemistry and Medicine, "Enzyme–Immunoassay: A Review," vol. 4, 109–143, Springer–Verlag Berlin Heidelberg, 1986.

Annals of Clinical Biochemistry, "Enzyme Immunoassay: A Review", Department of Biochemistry, University of Surrey, Guildford, vol. 16, pp. 221–238.

*Primary Examiner*—Carol A. Spiegel
*Attorney, Agent, or Firm*—Nikaido, Marmelstein, Murray & Oram

[57] ABSTRACT

Subject matter of the invention is a new method of detecting a substance with hydrolase activity in a sample, characterized in that the sample is brought into contact with an indicator enzyme, which is covalently bound to an insoluble carrier material and can be rendered soluble by the hydrolase activity, in that the cleaved off indicator is separated and in that its enzymatic activity is determined and test means for its implementation.

3 Claims, 1 Drawing Sheet

DEVICES FOR DETERMINING HYDROLASE ACTIVITY THROUGH ITS HYDROLYTIC RELEASE OF AN IMMOBILIZED INDICATOR ENZYME

Subject matter of the invention is a new method for determining the concentration of substances with hydrolase activity in a sample and means for implementing said method and a method for determining an analyte in a body fluid with the aid of a conjugate comprising a hydrolase and a substance capable of binding to the analyte and test means for said method.

In modern diagnostics, the determination of substances with hydrolase activity has gained increasingly more importance. This applies to tests for detecting hydrolases and to imunological tests.

In clinical diagnostics tests for detecting hydrolases in blood, for example, play an important role in the control of bodily functions.

Recently, imunological methods using hydrolases as labelling enzymes are used to determine the analyte concentration in body fluids. The presence of certain components allows conclusions on the state of health of the person examined. Often, metabolic disorders have direct effects on the concentration of individual metabolites. It is, therefore, important to have methods for the qualitative and quantitative analysis of metabolites.

Due to the different properties of the components, the analytical methods also have to differ greatly from one another. These test methods are often specifically geared toward one certain component. One often utilizes the properties of the components which are closely related to its function.

An enzyme for example, can be detected in body fluids by determining its enzymatic activity. This enzymatic activity is usually measured by adding a suitable substrate. In the course of the reaction, the UV-absorption of a reaction mixture changes as a consequence of formation or elimination of a UV-absorbing substance. This change in absorption can then be expressed in terms of concentration or concentration changes of the component to be analyzed.

In more recent methods. imunological steps are included in the analysis of components in body fluids. This applies particularly to the determination of haptens, antigens and antibodies. Imunological reactions are particularly distinguished by an exact stoichiometry of the underlying reaction between the imunological partners, namely hapten or antigen, on the one hand, and antibodies, on the other hand. Moreover. the use of monoclonal antibodies has greatly improved the specificity of the detections.

The expert is familiar with numerous variants of imunological assays, For practical purposes. a distinction is made between homogeneous and heterogeneous immunoassays. Whereas homogeneous methods are based on the fact that all detection reactions occur in solution. the immunologically reactive compounds (such as haptens, antigens, antibodies or immune complexes formed with these compounds) in heterogeneous methods are separated into two phases. While one part, for example the immunologically reactive component to be analyzed, is in solution at the beginning of the assay, another part may be adsorptively, covalently or precipitatively bound to an insoluble carrier material. Heterogeneous immunoassays are again subdivided into different variants from which the expert may select the most suitable variant depending on the analyte to be determined. An overview of the methods used in prior art is found in Hubbuch et al. (*Progress in Clinical Chemistry and Medicine*, Vol. 4, p. 109 et seq. published by Springer Verlag Berlin Heidelberg, 1986). Examples include:

Competitive Immunoassays

A sample containing the analyte in an unknown quantity is, together with a known quantity of the analyte which carries a label, brought into contact with an insoluble carder material to which an immune partner of the analyte is bound in the above described manner in a known quantity and in deficit. In the immune reaction a part of the analyte and also of the labelled analyte is bound so efficiently that it remains attached to the solid phase after the subsequent separation of liquid and solid phase. The amount of label measured at the solid phase or in the liquid phase in a detectable indicator reaction is a function of the concentration of the analyte to be determined. This concentration can be determined from the distribution of the label in the two phases.

An example describing such a competitive immunoassay is described in EP-B-75379

Non-Competitive Immunoassays a) The sample with an unknown quantity of analyte together with an excess amount of corresponding labelled immune panner is brought into contact with an even greater excess amount of analyte or analyte analog which is bound to a solid phase. The excess amount of immune panner which had not reacted with the analyte during the initial immune reaction is thus bound to the solid phase. After separation of the solid phase. the liquid phase contains a quantity of label which is proportional to the initial concentration of analyte.

An example for such an immunoassay is given in U.S. Pat. No. 4,446,232.

b) In yet another immunoassay, the sample with the analyte is brought into contact with an excess amount of corresponding immune partner which was bound to the solid phase in the above described manner. Subsequently, an excess amount of labelled immune partner which is specific to another part of the analyte is added. After the immune reaction, the excess of labelled immune partner is removed from the solid phase by washing. The amount of label measured at the solid phase is proportional to the amount of analyte contained in the sample. Such an example is described in U.S. Pat. No. 4,098,876.

In these imunological methods of determining an analyte haptens, antigens or antibodies may serve as analytes and antibodies; haptens and antigens as immune panners.

All of the above listed immunoassays are based on the determination of the concentration of an enzyme-labelled or radioactively labelled immunologically active compound which is present in a predetermined relation to the analyte concentration to be determined.

In order to determine the amount of enzyme label, a suitable indicator enzyme substrate is added to the solution which contains the characteristic amount of indicator enzyme. This indicator enzyme substrate is selected such that a change in its concentration is detectable.

This requirement is met in particular by those substrates which exhibit a characteristic light absorption. light emission of fluorescence or by substrates whose products resulting from the indicator reaction exhibit a characteristic light absorption. light emission or fluorescence. Sometimes hydrolases are also used as indicator enzymes. The substrates used in this case are. as in the detection of hydrolases, those compounds which can be cleaved by hydrolases under the addition of water. The result is a detectable product. An example for a substrate for the determination of the amount of labelling with/β-galactosidase as an indicator enzyme is chlorophenol red-β-D-galactoside of EP-A-0 146 866.

Small analyte concentrations also entail small amounts of label to be detected. Consequently, the activity of the indicator enzyme present in the sample and the amount of enzyme substrate which reacted per time unit are also very small. It, hence, takes time until a change in the concentration of the enzyme substrate is so pronounced that it can be detected. External influences (temperature deviations or the like) during the extended duration of the assay may increase the error rate of the measurement.

The problems encountered with small analyte concentrations can be reduced by using certain methods. The intensity of the signal, for example, generated by the change of the concentration of the substrate or the product of the indicator reaction which in turn was caused by the enzyme label, can be increased if the measurement distance in the detection of the electromagnetic radiation by applying of the law of Lambert and Beer is increased. This, however, requires the use of considerably larger sample volumes. On the one hand, the implementation of a method with such large sample volumes requires an instrument which is large and shows poor handling qualities.

On the other hand, it is often not possible nor desired to use larger sample volumes. This applies in particular to direct determinations of analytes in body fluids, where methods which use only one drop of liquid for the assay have proven to be particularly advantageous. In so-called dry-tests, e.g. according to DE-A-32 476 08 processes with large sample volumes can therefore not be used.

If an imunological assay method is selected where the amount of labelling is inversely proportional to the analyte concentration. the resulting error rate is rather high for very small analyte concentrations. The method in question is not recommended for such case.

With the above described assays. substances with hydrolase activity and, hence, analytes in body fluids can, depending on the assay used, be determined only up to a certain minimum concentration. However, body fluids contain components which are present in even smaller concentrations and whose determination is desirable. With conventional methods, the concentrations of these components can either not be measured at all or only with great inaccuracy.

In order to increase the sensitivity of imunoassays, EP-B-0 060 123 proposes the use of a reaction cycle which is triggered by a conjugate of alkaline phosphatase and an antibody. Due to the enzyme labelling, NADP is converted into AND; in the reaction cycle. alcohol dehydrogenase then reduces AND to NADH and tetrazolium salt oxidizes NADH under the formation of color back to AND. The drawback of this method is that it can not be used with whole blood as this contains itself considerable concentrations of phosphatases, dehydrogenases and NADH in various amounts. These substances falsify the detection of the conjugate. Another drawback of this method is that the great number of reagents such as enzyme substrates, enzymes or cofactors complicate the realization of this method and lead to stability problems.

EP-A-0 027 036 also proposes an amplification principle which encompasses two enzymatic systems. The disadvantage of this principle is that its second enzymatic system operates with enzymes that are widely distributed in body fluids where some of these enzymes are present in varying amounts. A fact which leads to false results. Moreover, it is not possible to stop this amplification reaction in a simple manner. Only one enzyme can be used in the indicator reaction.

It is, hence, an object of the present invention to provide a more sensitive method of determining the concentration of a substance with hydrolase activity, while avoiding the above mentioned disadvantages.

Surprisingly, it has been found that it is possible to significantly increase the sensitivity of methods for determining the concentration of substances with hydrolase activity. A measure for the increase in sensitivity is the amplification factor. The latter indicates how many mols of detectable units (e.g. color molecules) are released per mol of analyte.

Subject matter of the invention is, hence, a method for detecting a substance with hydrolase activity in a sample, characterized in that the sample is brought into contact with an indicator enzyme bound to an insoluble carrier material, wherein said indicator enzyme can be rendered soluble by the hydrolase activity: the cleaved indicator enzyme is then separated and the enzymatic activity is determined.

Further, the invention claims means for detecting a substance with hydrolase activity in a sample, said means comprising an indicator enzyme which is bound to an insoluble carrier material and can be rendered soluble by the hydrolase activity.

Substances with hydrolase activity are understood to be hydrolases themselves as well as soluble compounds of hydrolases with any other desired chemical substance.

Hydrolases include naturally occurring or artificially synthesized enzymes of main division 3. They are capable of cleaving characteristic substrates while consuming water. They include, e.g., esterases. peptidases, and glycosidases.

Particularly suitable hydrolases include conjugates with endo-enzymes, such as endoglycosidases, endopeptidases and the like. (The term endo-enzyme refers to enzymes which do not cleave from the end of the substrate for which they are specific). Conjugates consisting of carbohydrate cleaving enzymes such as dextranase, alginase, agarase, pectinase, cellulase or chitinase have proven to be particularly effective.

Compounds of hydrolases with other chemical substances include in particular combinations of hydrolases with immunologically active substances such as antigens, haptens or antibodies or immune complexes but also nucleic acids, such as DNA. These substances are hereinafter referred to as hydrolase-labelled compounds or hydrolase conjugates.

The first step of the method of the invention is to bring a sample which contains the substance with hydrolase activity into contact with an indicator enzyme which is bound to an insoluble carder material.

Preferably, the sample in which the substance with hydrolase activity can be detected, is understood to be an aqueous solution. These solutions can, for example, include solutions of a hydrolase or a hydrolase conjugate in water. These solutions often contain admixtures such as salt, detergents and the like to increase storage stability, for example. The method of invention can also be applied when assaying solutions of this type. The liquid sample can also be a body fluid or any other liquid obtained from such a body fluid by adding or separating components. Examples include blood, blood plasma, serum or urine.

A preferred liquid sample can also be a liquid as is produced in the course of immunoassays. They are described, for example, in *Annals of Clinical Biochemistry* (1979). 16:221, and advantageous further developments thereof are known to the expert in the field of immunoassays. In these methods, a conjugate consisting of a partner of a biospecific reaction, e.g. an antibody to the analyte to be detected in the test or to a competitive partner of the analyte, and a labelling enzyme, e.g.β-galactosidase, are used. In the determination reaction the concentration of the labelling enzyme in the resulting liquid is measured in terms of its enzymatic activity. In such liquids it is possible to detect substances with hydrolase activity, particularly conjugates of hydrolases with the above listed compounds, by using the method of the invention. Usually, these solutions contain buffer substances. stabilizing agents, wetting agents etc. which, however, do not interfere with the detection.

In this case, it is preferable to use hydrolase conjugates which are usually not found in body fluids. They include the above listed hydrolases, and more particularly, dextranase, alginase. agarase, pectinase, cellulase and chitinase. Dextranase is particularly preferred.

An indicator enzyme as understood in the invention is any enzyme whose enzymatic activity can be determined with one or several substrates for this enzyme. In particular, it is possible to use all known indicator reactions that are based on an enzyme-substrate reaction. They include, for example, reactions which produce a directly detectable product but also reactions which require an intermediate step to produce a detectable signal. The substrate used in reactions which are followed by an additional step can be a carrier material, for example, to which there is bound another indicator enzyme. Reactions which produce a color change or where a colored compound is formed or disappears have proven to be particularly useful. The expert is familiar with such enzymes and their corresponding substrates. Examples of indicator enzymes/substrates are β-galactosidase/β-galactoside, peroxidase/peroxide and phosphatases/phosphate. A particularly preferred indicator enzyme for such a test is an enzyme which is not contained in the sample at all or only in neglectable quantities and whose activity differs from the activity of the substance with hydrolase activity. Suitable indicator enzymes are those whose substrate specificity differs from the one of the substance which exhibits hydrolase activity.

Further, preferred indicator enzymes are those whose substrate specificity is not substantially impaired by the substance with hydrolase activity. The question of whether or not this is actually the case can be answered by the expert. if necessary in some few experiments. β-galactosidase, for example, has proven well as an indicator enzyme if dextranase is the substance with hydrolase activity, to be detected.

Prior to adding the sample containing the substance with hydrolase activity, this indicator enzyme is bound to a carder material which is insoluble in the sample and thus immobilized and, consequently, also rendered insoluble.

The carrier material and the manner of binding the indicator enzyme to the carder material are selected such that the indicator enzyme, as a consequence of the effect of the substance with hydrolase activity, is released and rendered soluble. The following are particularly preferred cases:

The carrier material is selected such that it can be completely or partially hydrolyzed by the substance with hydrolase activity. In this case, the carder material selected is a substrate of the hydrolase contained in the substance with hydrolase activity. Since the carder material is degraded, the indicator enzyme which was bound to the latter is released and dissolves in the reaction liquid.

Long-chain polysaccharides or polysaccharide analogs, particularly dextran, dextran sulfate, alginic acid, agarose, pectins, pectic acids, chitin and carboxymethyl celluloses have proven well as carrier materials. Long-chain peptides could be used for endopeptidases. In this case, it must be ensured that the endopeptidases do not attack the indicator enzyme itself.

The term dextranes refers to polysaccharides conventionally known as dextran and to modified and cross-linked dextran such as Sephadex®. Modified dextran are those with additionally incorporated functional groups such as amino or carboxyl groups, for example. They are obtained by partial oxidization of the dextran with potassium periodate and reaction with 1, n-diaminoalkanes. especially 1, 6-diaminohexane, bivalent acid amides, especially succindiamide or 1. n-aminoalkanoic acids, especially 6-aminohexanoic acid, followed by a reduction reaction with sodium borohydride, for example.

This allows introduction of additional cross-linking of the dextran to further reduce their solubility, for example. Preferred dextran or dextrane sulfates have a molecular weight of appr. 40,000 D to 500.000 D, a particularly preferred molecular weight ranges between 110,000 D to 250,000 D, and following a cross-linking between $20 \times 10^6 D$ and $500 \times 10^6 D$.

Dextran, pectin- or cellulose cleaving enzymes such as dextranase, pectinase, alginase and agarase are, therefore, particularly well suited as substances with hydrolase activity.

Other suitable carder materials are compounds of the above listed materials with other inorganic or organic carrier materials, for example polyamides. polyesters and silanized titanium dioxide. If dextran compounds are used as carder materials, the above described dextrans can be used, with a particularly advantageous molecular weight ranging between $100 \times 10^6 D$ and $500 \times 10^6 D$. The substances with hydrolase activity are also the ones listed above.

These carrier materials can either be purchased or are otherwise available to the expert in a familiar way.

Polyester-containing carder materials can be produced, for example, by saponification of the ester groups of the polyester, activation with N-hydroxy succinimide and reaction with the above listed dextrans, dextran sulfate etc.

Polyamides or titanium dioxide silanized with triethoxysilylpropylamine can be coupled to the dextran or dextran sulfates etc. via the free -NH$_2$-groups.

The coupling of inorganic or organic carder materials to dextran can also be accomplished by partial oxidization of the dextran with potassium periodate followed by reaction with inorganic or organic carder materials.

The indicator enzyme can be coupled to the so obtained dextran-or dextran sulfate-containing carrier materials and to the carrier materials consisting exclusively of dextran or dextran sulfate in the following manner:

the carrier materials are activated with potassium periodate and reacted with the indicator enzyme the carrier materials are reacted with a coupling reagent and the indicator enzyme the carrier materials are reacted with benzoquinone or derivatives thereof, e.g. chloroamide and subsequently reacted with the indicator enzyme.

free amino groups of the modified dextranes are activated with the aid of 3-maleimidobenzoyl-N-succinimide (MBS) and coupled to the indicator enzyme, particularly via its sulfhydryl residues.

The insoluble carrier material to which the indicator enzyme is coupled may be present in any desired form, for example as tissue, fleece, powder, particles or as a vessel.

The quantity indicator enzyme dissolved in the reaction liquid per time unit is proportional to the amount of substance with hydrolase activity contained in the reaction liquid and, hence, in case of an immunoassay also to the concentration of the analyte in the sample. A prerequisite is that the amount of indicator enzyme bound to the carder material suffices to provide a sufficient amount of cleavable indicator enzyme. An expert is able to determine the necessary amount of carder material with indicator enzyme in a few simple tests.

The indicator enzyme which is dissolved in the reaction liquid is subsequently separated from the indicator enzyme which is bound to the insoluble carrier material. This is achieved in a particularly simple manner by removing the reaction liquid, for example, by means of vacuum suction, pipetting, filtering, decanting, centrifuging or the like.

Thus, it is no longer possible that any more indicator enzyme is rendered soluble in the separated reaction fluid by substance with hydrolase activity which may eventually be dissolved in the reaction fluid. This is an advantage since the reaction can thus be stopped at a given time in an especially simple manner.

In order to determine the amount of free indicator enzyme contained in the solution which was separated from the carrier material, said solution is, at a given time, added to a suitable substrate under conditions which are constant for each indicator enzyme and also known to the expert. The amount of substrate consumed or product formed is later measured at a given time. EP-A-0 146 866 describes an example of such a detectable indicator reaction for β-galactosidase.

When using chromogenic substrates, the course of the reaction can be visually monitored. It is feasible to perform a quantitative analysis with the aid of instruments. for example photometers such as fluorescence or reflectance photometers.

The concentration of free indicator enzyme is an exactly determined measure for the amount of substance with hydrolase activity.

In order to correlate the result of the indicator reaction with a certain concentration of substance with hydrolase activity, it is preferable to establish a calibration curve of samples with different but known concentrations under the same conditions.

After obtaining a result from the indicator reaction under the same conditions using a sample with an unknown concentration, the concentration to be determined can be directly read off the calibration curve.

An important condition for correct results is to avoid, if possible, contact between the substrate used in the indicator reaction and indicator enzyme still bound to carrier material. This is usually accomplished by spatially separating free indicator enzyme from bound indicator enzyme according to the invention. Moreover, the reliability of the results can even be further increased if the substrate, to which the solution containing the indicator enzyme is added, is bound to a solid matrix. This matrix can be a reagent film or tissue, paper or particles.

The substrate is bound such that the reaction with the indicator enzyme is essentially not negatively affected. This can be accomplished by linking the substrate via spacers, for examples. However, the substrate and the reagents necessary for the reaction may also be present in solution, in a dry form, as a coating on a matrix or as a mixture with substances which lead to a solid state of aggregation of the mixture. These substances, known as "structure forming agents", allow easy handling and dosing of the mixture.

The method is carried out under conditions optimized to match the reactions involved, in particular the enzymatic reactions.

The temperature is selected such that the enzymes are not inactivated while the reaction rate is still sufficiently high. The preferred temperature range is between 18° C. and 42° C., particularly between 25° C. and 37° C.

The pH value of the individual reaction steps can be equal or different. Since all participating enzymes have a certain optimal pH, it is advantageous to work in the vicinity of this value. The optimal pH of dextranase, for example, is at 6.0, the one of pectinase at 4.0, for cellulase it is at 5.0 and for β-galactosidase at 7.4. The pH range still allowing a sufficiently fast rate is, hence, between 3.0 and 9.0, particularly between 3.5 and 8.0. It is. however, also possible to optimize the pH for each reaction step by changing the buffer correspondingly.

As the method of the invention is very sensitive, it is also possible to carry out very rapid concentration determinations. The rate of the method increases with an increasing amplification factor. Generally speaking, a determination can be carried out in less than 1 hour, preferably in less than 10 min.

The sensitivity of the method of the invention is such that, under normal conditions, even concentrations of up to $10^{-12}$ mol/l of a substance with hydrolase activity can be detected within 10 min. It is, of course, also possible to detect higher concentrations in which case the results are available within a shorter period of time. This is of great advantage for clinical diagnostics.

Further advantages of the method of the invention include its simple implementation: then, the fact that it involves only a small number of components, i.e. the indicator enzyme bound to the carrier material and a substrate for the indicator enzyme which produces a measurable signal in the indicator reaction, which accounts for increased stability and reduces the chance of secondary reactions; further, the fact that by selecting a certain indicator reaction, the method can be adjusted such that other components of, for example, the body fluid do not affect the reaction in an unexpected manner.

The method of the invention is particularly suited to be used on so-called test strips. Test strips basically consist of a base plate or foil to which the reagents necessary for the assay are attached via fleeces or films. The carrier material to which the indicator enzyme is bound is advantageously configured as a fleece onto which the sample to be tested is applied. Another fleece or film holds the reagents necessary for the indicator reaction. In this fleece, the test can be immediately evaluated either visually or photometrically.

Advantages include, for example, that the method is simple and inexpensive and yet provides reliable results.

The method can also be carried out as a so called wet test. In such a wet test, the individual reaction steps are carded out in one or several tubes (reaction vessels, cuvettes). the reagents being preferably added in the form of solutions. At least one solid phase is in any case necessary, i.e. the one of the above mentioned carder material with the indicator enzyme bound to it. The latter can be coated to the tube wall, for example, or be used in the form of particles.

The method of the invention of detecting a substance with hydrolase activity can particularly be used in assays such as immunoassays for the detection of an analyte. The expert in the field of immunoassays is familiar with such methods (e.g. *Annals of Clinical Biochemistry*(1979). 16:221). These methods are modified in that the indicator enzyme conjugate is replaced by a hydrolase conjugate, and the required detection of the conjugate is then determined with the method of the invention.

The expert is either familiar with methods relating to the synthesis of enzyme-labelled and hydrolase-labelled immune partners such as haptens, antigens, antibodies and antibody fragments or is able to carry out these methods in analogy to known methods.

Analytes are understood to be haptens, antigens and antibodies. Haptens are substances with a relatively low molecular weight which are recognized by antibodies but are not capable of inducing an immune response by themselves. Examples for haptens include endogenous substances such as thyroxine (T4), triiodothyronine (T3), or therapeutically active compounds such as digoxin, theophylline or drugs (narcotics).

Antigens are proteins which are recognized by antibodies and are capable of inducing an immune response. These proteins can be naturally occurring or artificially synthesized substances. Antigens also include antibodies which are recognized by another antibody as an antigen. Antigens whose determination in body fluids is of importance are e.g. thyrotropin (TSH), follicle-stimulating hormone (FSH), luteinizing hormone (LH), hemoglobin (Hb), human choriogonadotropin (hCG), immunoglobulin G. human serum albumin (hSA), carcinoembryonic antigen (CEA), alpha-foetoprotein (AFP) and also enzymes. Further, antigens include natural derivatives of proteins, for example. glycoproteins or artificially produced compounds consisting of proteins and other chemical compounds.

Antibodies are understood to be immunoglobulins capable of binding an antigen or hapten as defined above.

In case the analyte is an antigen or hapten, the following methods have proven particularly well:

An excess amount of conjugate solution comprising an antibody to the analyte (analyte-specific substance) and a hydrolase is added to the sample solution which contains the analyte to produce an immune complex consisting of analyte and conjugate. In an immune reaction, the excess conjugate is bound to a carrier to which there is bound an excess amount of analyte or of an analyte-analog compound. An analyte-analog compound is a compound whose interactions, e.g. immunological reactions, with the reaction partners are similar to those of the analyte. The general structure of an analyte analog is only slightly different from the one of the analyte. An analyte-analog compound can also be an antiidiotypical antibody.

Anti-idiotypical antibodies are directed against the antigen binding site of an antibody and react with this binding site in the same manner as the analyte. The solution containing the conjugate of hydrolase and immune complex is separated from the carder and subject to the method of the invention. From the test result obtained for the hydrolase conjugate conclusions can be drawn on the presence and the quantity of analyte. This embodiment is particularly preferred as it does not require exact metering of the conjugate and the carder material. The preferred antibody is a monoclonal antibody. Particularly preferred are fragments, for example the Fab fragment. The Fab:enzyme stoichiometry ranges between 1:2–1:4.

An amount of conjugate comprising an antibody to the analyte (analyte-specific antibody) and a hydrolase is added to the sample solution containing the analyte. said amount being in excess to the amount of analyte expected to be present. The amount of conjugate is known. The resulting product is an immune complex consisting of analyte and conjugate. The remaining excess amount of conjugate is bound in an immune reaction to a carder to which there is bound an excess amount of an antibody to the analyte (analyte-specific substance) which recognizes another binding site of the analyte than the antibody of the conjugate. The solution containing the excess amount of conjugate of hydrolase and antibody is separated from the carder and the conjugate of antibody and hydrolase contained in the solution is detected in accordance with the method of the invention.

A known amount of conjugate comprising analyte or analyte analog and a hydrolase is added to the sample solution containing the analyte. The mixture is applied onto a carder to which there is bound a known deficit amount of an antibody to an analyte (analyte-specific substance) and the analyte analog, this deficit amount being based on the sum of analyte and conjugate.

A part of the analyte and of the conjugate is bound to the carder. According to the method of the invention, the conjugate contained in the solution can be detected once the solution is separated.

The same principles apply if the analyte is an antibody; the antibody mentioned in the above described method, however, must be replaced by an antigen or an antibody to said antibody.

In immunological tests for the detection of an analyte, the detection of the hydrolase conjugate in accordance with the invention is followed by an evaluation procedure. The presence or, in case of a quantitative evaluation, the amount of analyte present in the original sample can be concluded from the presence or the amount of detected hydrolase conjugate. This can be done via a calibration curve, for example.

The advantages of the method of the invention of detecting a substance with hydrolase activity will also be effective in this immunological method of detecting an analyte. It is a particular advantage that the substance with hydrolase activity exhibits a hydrolase activity which is not contained in the solutions to be assayed. Having an amplification effect which can be triggered with very simple means, the method of the invention is also suited for analytes which are present in samples, e.g. body fluids in only minor quantities.

This immunological test can also be advantageously used in connection with test strips.

The method of the invention can analogously also be applied in methods of detecting nucleic acids with the aid of enzyme-labelled nucleic acids, e.g. nucleic acid hybridization tests. The enzymatic label is then a hydrolase which is detected by applying the method of the invention. Nucleic acid means in particular DNA.

Another subject matter of the invention is a method of detecting or determining an analyte in body fluids using a conjugate comprising a labelling enzyme and a substance capable of binding to the analyte. The labelling enzyme used is a hydrolase which does normally not occur in the body fluid. A certain amount of this hydrolase conjugate, said amount being characteristic for the amount of analyte, is brought into contact with an indicator enzyme bound to an insoluble carrier material. As a consequence of the effect of the hydrolase, the indicator enzyme is also cleaved off in dependency upon the quantity of analyte. Then the cleaved off indicator enzyme is separated from the carrier material and the activity of this indicator enzyme is determined.

Yet another subject matter of the invention are means for determining the concentration of a substance with hydrolase activity in a liquid sample.

These means include all reagents necessary for implementing the method of the invention for determining the concentration of the substance with hydrolase activity. The means comprise in particular an indicator enzyme bound to an insoluble carder material which can be rendered soluble through said hydrolase activity.

Said means suitably further comprise the reagents necessary for determining the concentration of the indicator enzyme. The reagents contain, for example, an indicator enzyme substrate.

Indicator enzyme substrates are compounds which produce a detectable change which is catalyzed by the indicator enzyme. In a preferred manner, they can be cleaved or are part of an oxidization-reduction (redox) system. The substrate or the product of its reaction with the indicator enzyme is detected colormetrically, fluorometrically or in an electrochemical process. Examples of such substrates are $\beta$-galactosidase, the galactosides of resorufin. chlorophenolate or nitrophenol. Examples for peroxidase substrates are resorufin and triarylimidazole.

Moreover, if necessary the means can also contain pH buffering substances, stabilizers, activators etc.

The kind of indicator enzyme substrate and all other components depend upon the indicator enzyme to be determined and are known to the expert. If, for example, $\beta$-galactosidase is used as an indicator enzyme. the reagents listed in EP-A-0 146 866 can be used.

Before or during the method of the invention. the reagents used for determining the concentration of the indicator enzyme are preferably kept separate from the indicator enzyme bound to the carrier material in order to avoid a false indicator reaction.

The means of the invention can contain the indicator enzyme which is bound to the insoluble carrier material in various forms; including, for example, suspension, powder, fleece. tissue, vessel, tablet etc., if necessary, together with known carrier substances.

The reagents of the means of the invention which are necessary for the indicator reaction can be made available in the form of powder, as a tablet, a solution or impregnated on a fleece, tissue etc.

Figure 1:
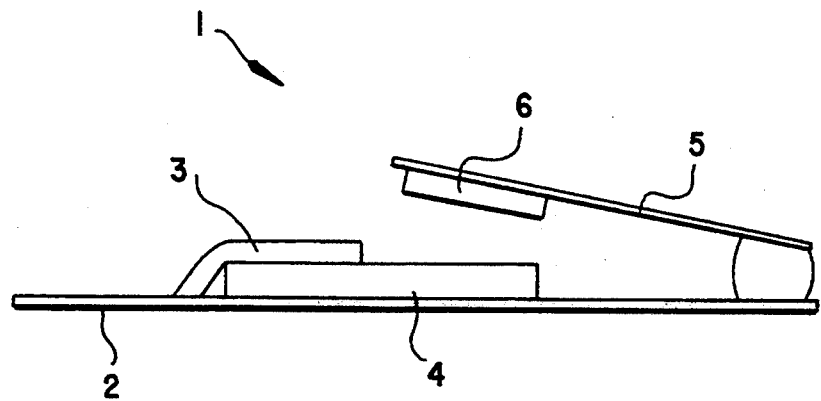
FIG. 1 is a diagram of the device of the invention. Element 2 is the base foil, element 3 is the fleece to which the sample is applied, element 4 is the carrier material to which the indicator enzyme is bound, element 5 is the flap which causes the different layers to be brought into contact, and element 6 is the fleece containing the indicator enzyme detection system.

A preferred first embodiment of the means in the form of a test strip is shown in FIG. 1. The test strip comprises several layers which the sample may traverse. The purpose of the layers is to either separate substances in the sample, incubate with reagents, transport or monitor reactions. Said layers are preferably in contact with one another in such a manner that the sample advances from one layer to the next be means of capillary forces. Fleece 3 serves to separate interfering sample components such as erythrocytes when testing a blood sample (DE-A-3029579). It is also the site of sample application. Reference numeral 4 designates the carrier material to which the indicator enzyme is bound. When determining substances with dextranase activity, this is, for example, a alextrane to which an indicator enzyme is bound. The sample having traversed fleece 3 is distributed in this zone while a pan of the indicator enzyme is cleaved from the carrier material under the influence of the substance with hydrolase activity and then goes into solution. After pushing down flap 5, which holds the substrate fleece 6, onto the carrier material 4, which rests on the base foil 2, the reaction solution penetrates the substrate fleece 6 and the indicator reaction is allowed to start.

The means of the invention for determining the concentration of an analyte comprise all components of the above described means for determining the concentration of a substance with hydrolase activity. In addition, said means comprise substances which allow the release of an amount of substance with hydrolase activity which is characteristic for the analyte concentration to be determined. The expert can employ these reagents in analogy to known methods.

Another subject matter of the invention are test means for detecting an analyte in a liquid sample, said test means comprising several layers which the sample may traverse and which are attached to a solid carrier, characterized in that said test means comprise the following in the order given below:

- a layer containing a conjugate of an antibody to an analyte and a hydrolase which is not present in the sample,
- layer containing immobilized analyte or immobilized analyte analog,
- a layer containing an indicator enzyme bound to an insoluble carrier material, said indicator enzyme being rendered soluble in that it is brought into contact with a hydrolase,
- a layer containing the reagents necessary for the detection of the indicator enzyme, while each layer is or can be brought into contact with the adjacent layer.

Figure 2:
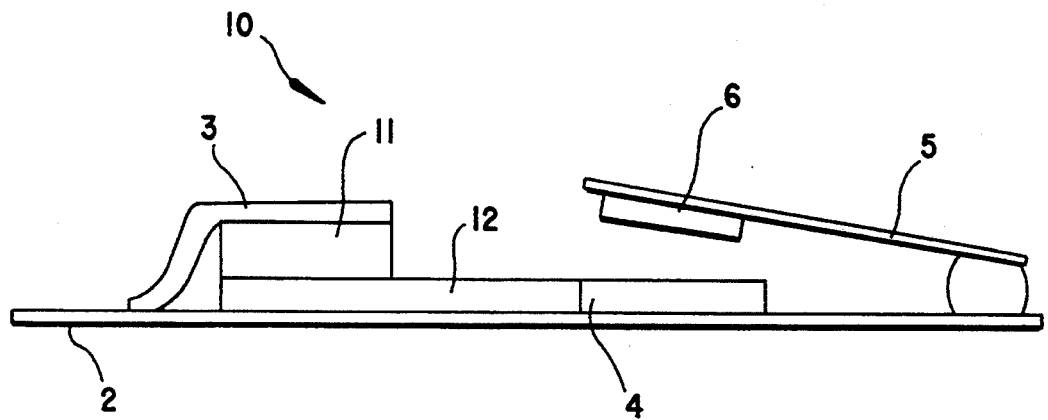
FIG. 2 is a diagram of a second embodiment of the device of the invention. In addition to the elements of FIG. 1, the device of FIG. 2 contains element 11 which is a fleece which contains an immune partner of the analyte to be determined which is labeled with a hydrolase and element 12 is a fleece which contains a matrix to which the analyte or analyte analog is bound.

An embodiment of such test means is shown in FIG. 2. It relates to a so-called immunoenzymometric assay. In addition to the above described embodiment 1, test strip 10 of this embodiment contains the additional fleeces 11 and 12. An amount of conjugate comprising an immune partner of the analyte to be determined. which is labelled with a hydrolase, is impregnated on fleece 11, the amount of conjugate being in excess to the analyte. Fleece 12 contains a matrix to which the analyte or analyte analog is bound in excess.

In order to determine the concentration of an analyte in a sample, the sample is applied onto fleece 3. Once the solution has penetrated fleece 11, the conjugate contained in the latter is removed therefrom and reacts with the analyte contained in the sample in an immune reaction. The solution with the so formed immune complex and the excess amount of conjugate penetrates fleece 12. In the latter, the excess amount of conjugate is removed from the solution in the course of an immune reaction with the matrix-bound analyte or analyte analog. The solution with the immune complex, which is the substance with hydrolase activity, enters fleece 4 and is determined as described above. The amount of substance with hydrolase activity is directly proportional to the amount of analyte in the sample.

Moreover, the test means shown in FIGS. I and 2 may contain, if advantageous to the implementation of the method, additional components, in particular fleeces or tissues which may carry a reactive coating. The arrangement of the fleeces can be selected accordingly by the expert.

Advantageously, the method of the invention is applied on automated analyzers since this ensures fast results and good reproducibility.

The following examples explain the invention in greater detail.

EXAMPLE 1

Preparation of a compound for determining the Concentration of dextranase or a dextranase conjugate A) Preparation of β-galactosidase bound to insoluble dextrane
   a) Preparation of oxidized dextrane
   50 mg of dry insoluble dextrane (characterization: Sephadex ®6200 (dry insoluble dextrane) are soaked in 10 ml redistilled water for 2 hours at 90° C. The deposited gel is reacted with 2 ml potassium periodate solution (15 mmol/l in redistilled water) for 30 min at room temperature and under shaking. The resulting gel is washed five times with 10 ml 50 mM potassium phosphate buffer (pH 8.5) and filtered in a glass frit.

b) Coupling
   25 mg β-galactosidase (Boehringer Mannheim GmbH) are dissolved in 0.5 ml potassium phosphate buffer (50 mM, pH 8.5) and 1 ml oxidized dextrane from a) is added. Coupling is carded out at 4° C. overnight on a roller agitator.

c) Reduction of the azomethine compound
   After coupling, the gel is washed with 100 mM sodium borate buffer (pH 8.5) and reduced with 1 ml sodium borohydride solution (5 mg/ml in 100 mM sodium borate buffer, pH 8.5) at 0° C. for 1 hour. Subsequently, the gel is washed with Tween buffer (10 mM sodium phosphate buffer, pH 7.0; 25 mM sodium chloride; 0.05% Tween ®20polyethoxy sorbitanlaurate) until there is no more β-galactosidase activity left to be measured.

B) The substrate solution is a 2 mM solution of 2-nitrophenol-β-galactoside

EXAMPLE 2

Determination of the concentration of dextranase or dextranase conjugate in a sample solution The sample solutions were a $2 \cdot 10^{-11}$M and a $2 \cdot 10^{-12}$M solution of dextranase or dextranase conjugate (dextranase = 1,6-Glucan-glucanohydrolase: EC 3.2.11 manufactured by Miles, specific activity 1700 U/mg) in Tween ® buffer (100 mM potassium phosphate. pH 6.0; 0.05 Tween ®20:5 mg/ml Crotein ®C water soluble proteine hydrolysate of an approximate molecular weight of 10,000).

The test was carried out by mixing 1000 μ-galactosidase as prepared in example 1A) and bound to insoluble dextrane and 100 μof the sample solution and then shaking the mixture for 10 min at 37° C. Subsequently, the suspension was centrifuged and, using 500 mM potassium phosphate buffer. the supernatant was adjusted to a pH of 8.5.

1 ml substrate solution was added to 0.1 ml supernatant and absorption was measured at 37° C. in comparison to a reference solution (without dextranase or dextranase conjugate being added) which was subject to the same treatment.

Example 3

Determination of the amplification factor

Amplification factor is defined as the ratio between the amount of β-galactosidase that was released due to the effect of the dextranase or the conjugate of the carder material coupled to β-galactosidase as described in example 1 a) and the amount of dextranase used.

$$V = \frac{\text{activity (units) of } \beta\text{-galactosidase released}}{\text{activity of dextranase conjugate used}}$$

Activity is defined as the conversion of substrate per time unit. The amplification factor was determined in analogy to example 2, the incubation period being varied.

| Period of incubation | Amplification factor |
|---|---|
| 5 min | 850 |
| 10 min | 1650 |

-continued

| Period of incubation | Amplification factor |
| --- | --- |
| 15 min | 2500 |
| 20 min | 3300 |
| 25 min | 4100 |

We claim:

1. A device for detecting an analyte in a fluid sample, said device comprising on a solid support several layers which fluid can traverse, wherein each layer is or can be brought into contact with an adjacent layer, said layers being in the following order:
   a) a first layer containing a conjugate of an antibody which specifically binds to the analyte or analyte analog and a hydrolase which is not present in the sample,
   b) a second layer containing immobilized analyte or analyte analog,
   c) a third layer containing an indicator enzyme which is different from the hydrolase of the conjugate of a) bound to an insoluble carrier material wherein the carrier material can be completely or partially hydrolyzed by the hydrolase of a), such that the indicator enzyme which was bound to the carrier material is released, and dissolves in the fluid,
   d) a fourth layer containing an indicator enzyme detection reagent.

2. A device for detecting an antibody in a fluid sample, said device comprising on a solid support several layers which fluid can traverse, wherein each layer is or can be brought into contact with an adjacent layer, said layers being in the following order:
   a) a first layer containing a conjugate of an antigen or hapten which specifically binds to said antibody and a hydrolase which is not present in the sample,
   b) a second layer containing immobilized antibody or antibody analog,
   c) a third layer containing an indicator enzyme which is different from the hydrolase of the conjugate of a) bound to an insoluble carrier material wherein the carrier material can be completely or partially hydrolyzed by the hydrolase of a), such that the indicator enzyme which was bound to the carrier material is released, and dissolves in the fluid,
   d) a fourth layer containing an indicator enzyme detection reagent.

3. The device of claim 2, wherein each layer comprises a capillary fleece material and fluid movement between the layers is by capillary action.

* * * * *